United States Patent
Deshpande et al.

(10) Patent No.: US 10,184,929 B2
(45) Date of Patent: Jan. 22, 2019

(54) SYSTEM TO DISTINGUISH BETWEEN X SPERM AND Y SPERM

(71) Applicant: Satish Deshpande, Guelph (CA)

(72) Inventors: Satish Deshpande, Guelph (CA); Donald Franklin Moyer, Chicago, IL (US); Bethany Naomi Deshpande, Quebec (CA)

( * ) Notice: Subject to any disclaimer, the term of this patent is extended or adjusted under 35 U.S.C. 154(b) by 0 days.

(21) Appl. No.: 15/424,988

(22) Filed: Feb. 6, 2017

(65) Prior Publication Data
US 2017/0146508 A1    May 25, 2017

Related U.S. Application Data

(63) Continuation-in-part of application No. 14/106,837, filed on Dec. 15, 2013, now abandoned.

(51) Int. Cl.
*G01N 33/487* (2006.01)
*G01N 21/47* (2006.01)
(Continued)

(52) U.S. Cl.
CPC ....... *G01N 33/487* (2013.01); *G01N 15/1012* (2013.01); *G01N 15/1459* (2013.01);
(Continued)

(58) Field of Classification Search
CPC .......... G01N 21/47; G01N 2021/4704; G01N 2021/4707; G01N 2021/4709; G01N 2021/4711; G01N 2021/4726; G01N 33/5005; G01N 15/10; G01N 15/14; G01N 15/0205; G01N 15/1459; G01N 15/1456; G01N 15/1463; G01N 15/1012; G01N 2015/1438; G01N 2015/1488; G01N 2015/1493; G01N 2015/1495; G01N 2015/1497; G01N 2015/107; G01N 2015/1093; G01N 2015/1081; G01N 2015/1006; G01N 2015/03; G01N 2015/035; G01N 2015/0238; G01N 2015/0288; G01N 2015/0294; G01N 33/487; G01N 15/1429; G01N 2015/149
See application file for complete search history.

(56) References Cited

U.S. PATENT DOCUMENTS 7,758,811 B2    7/2010  Durack et al.
2002/0186375 A1* 12/2002 Asbury .............. G01N 15/1434
                                                        356/440
(Continued)

OTHER PUBLICATIONS

United States Patent and Trademark Office, Office Action on U.S. Appl. No. 14/106,837, dated Apr. 9, 2015.
(Continued)

*Primary Examiner* — Gordon J Stock, Jr.
(74) *Attorney, Agent, or Firm* — Gowling WLG (Canada) LLP; Jeffrey W. Wong

(57) ABSTRACT

Approximations to distinguish between X sperm and Y sperm are obtained by detecting light scattered into a pre-set angular range. The scattered light is scattered in turn by nuclei of sperm moving single-file in a sample container. The sperm are not modified prior to the light scattering and are not modified by the light scattering. Approximations are improved by at least a second detection of scattered light.

1 Claim, 2 Drawing Sheets

(51) Int. Cl.
*G01N 15/14* (2006.01)
*G01N 33/50* (2006.01)
*G01N 15/10* (2006.01)

(52) U.S. Cl.
CPC ......... *G01N 21/47* (2013.01); *G01N 33/5005* (2013.01); *G01N 15/1429* (2013.01); *G01N 2015/1006* (2013.01); *G01N 2015/149* (2013.01)

(56) References Cited

U.S. PATENT DOCUMENTS

| | | | |
|---|---|---|---|
| 2004/0053243 A1* | 3/2004 | Evans | A61D 19/00 435/6.19 |
| 2005/0105077 A1* | 5/2005 | Padmanabhan | G01N 15/1484 356/39 |
| 2005/0112541 A1 | 5/2005 | Durack et al. | |
| 2006/0263829 A1* | 11/2006 | Evans | C12N 5/0612 435/7.2 |
| 2008/0153087 A1* | 6/2008 | Frontin-Rollet | C12N 5/061 435/6.18 |
| 2010/0167336 A1 | 7/2010 | Son et al. | |
| 2010/0240062 A1 | 9/2010 | Brawley et al. | |
| 2012/0122084 A1 | 5/2012 | Wagner et al. | |
| 2012/0202237 A1 | 8/2012 | Sedoglavich et al. | |
| 2013/0252237 A1* | 9/2013 | Wagner | G01N 15/14 435/6.1 |
| 2014/0091014 A1 | 4/2014 | Wagner et al. | |
| 2014/0256032 A1* | 9/2014 | Wooder | G01N 15/06 435/288.7 |
| 2014/0273192 A1 | 9/2014 | Sharpe et al. | |
| 2014/0309782 A1 | 10/2014 | Sharpe et al. | |
| 2015/0168297 A1* | 6/2015 | Deshpande | G01N 33/5005 356/338 |

OTHER PUBLICATIONS

United States Patent and Trademark Office, Final Office Action on U.S. Appl. No. 14/106,837, dated Nov. 19, 2015.
United States Patent and Trademark Office, Office Action on U.S. Appl. No. 14/106,837, dated Mar. 24, 2016.
United States Patent and Trademark Office, Final Office Action on U.S. Appl. No. 14/106,837, dated Oct. 6, 2016.

* cited by examiner ated with the first detector. TP$_1$ is an abbreviation used to

SYSTEM TO DISTINGUISH BETWEEN X SPERM AND Y SPERM

CROSS-REFERENCE TO OTHER APPLICATIONS

This application is a continuation-in-part of U.S. patent application Ser. No. 14/106,837, filed Dec. 15, 2013, which is hereby incorporated in full by reference. U.S. Provisional Patent Application No. 61/737,808, filed Dec. 16, 2012, is hereby incorporated in full by reference.

FIELD OF DISCLOSURE

This disclosure relates to the distinguishing of mammalian sperms cells without the use of marker agents (such as dyes, antibodies, etc.) to allow for the selection of gender of the resulting offspring.

SUMMARY OF THE DISCLOSURE

It is a new result and unexpected discovery that an approximation that a sperm is an X sperm (X chromosome resulting in a female offspring) rather than a Y sperm (Y chromosome resulting in a male offspring) can be obtained by detecting light scattered by the sperm into a preset angular range.

It is a new result and unexpected discovery that the approximation that the sperm is an X sperm rather than a Y sperm can be improved by detecting second light scattered by the sperm into a second preset angular range.

This can be done in-turn for each sperm in a single-file flow of sperm. Sperm likely to be X sperm according the approximation can be routed to an X sperm flow and sperm likely to be Y sperm according to the approximation can be routed to a Y sperm flow. Alternatively, unwanted sperm can be destroyed in the flow.

Sperm are not modified prior to the light scattering and are not modified by the light scattering.

BRIEF DESCRIPTION OF THE DRAWINGS

Embodiments of the present disclosure will now be described, by way of example, only with reference to the attached Figures.

DETAILED DESCRIPTION

Figure 1:
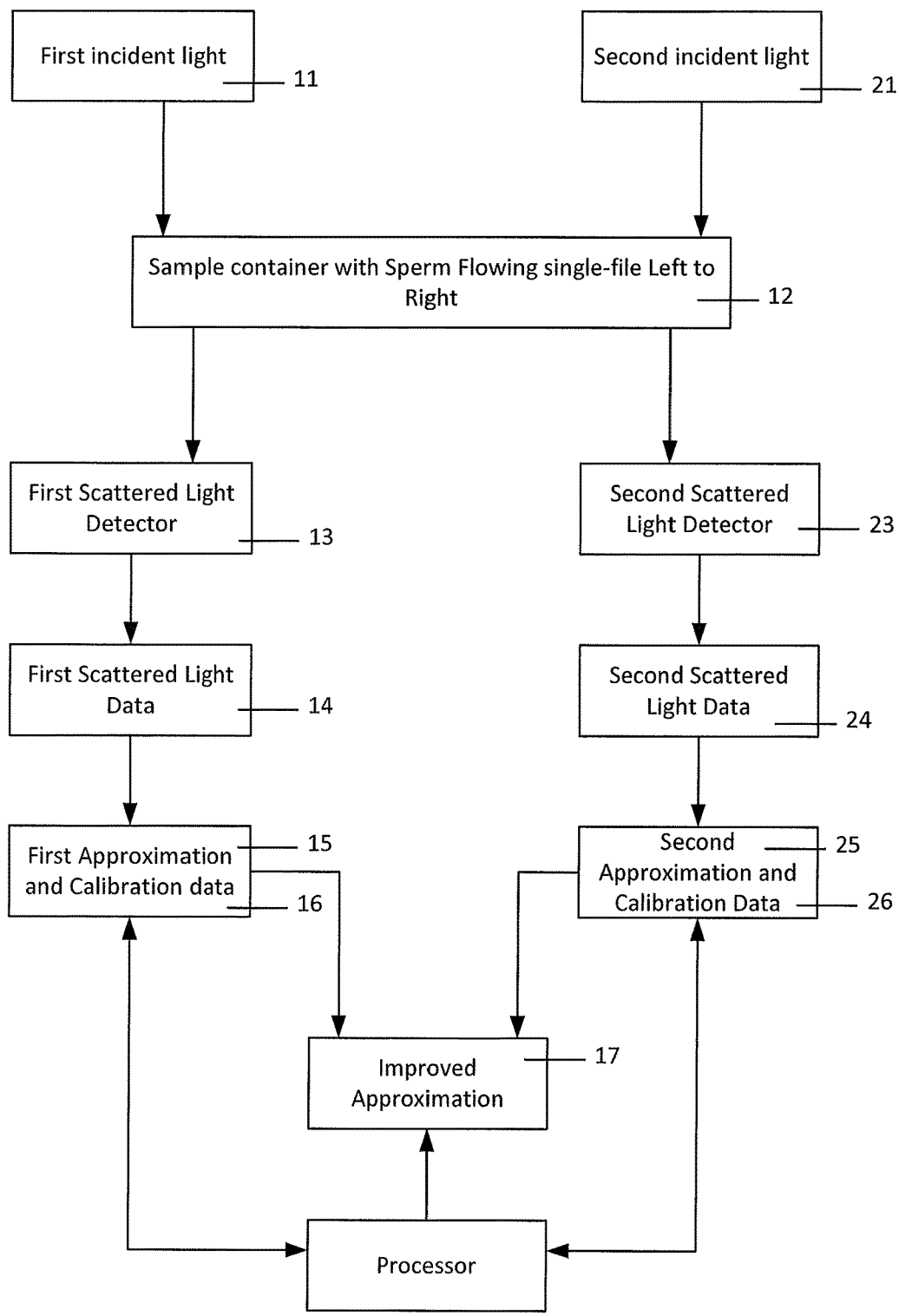
FIG. 1 schematically illustrates elements of the system.

Elements of a system to distinguish X sperm from Y sperm are illustrated schematically in FIG. 1.

The system comprises a first source of first incident light 11. The first incident light has a first incident light central ray. The first incident light has a first incident light wavelength. A 780 nm laser provides good data.

The system also comprises a sample container 12 to contain a test sperm from a sample of sperm. The test sperm and other sperm from the sample of sperm flow single-file along the sample container.

The sample container bore is just large enough for one sperm. The test sperm, typically contained in a chemical solution (also known as a sperm extender) which reduces or prevents degradation of the sperm, can be moved by a micro-fluidic actuator to a first detection part of the sample container and then moved on after detection.

The sample container is traversed by the first incident light central ray at the first detection region.

The system also comprises a first scattered light detector 13. The first scattered light detector is positioned to detect first incident light scattered by the test sperm in the sample container. In one embodiment, the light detector can be a webcam, such as with a resolution of 1280×720 pixels with adjustable settings for acquisition (i.e. brightness, exposure, gain, etc), as it provides good data quality to detect scattering. Other resolutions can be equally effective. The webcam is controlled by a processor such as a computer which also processes the image acquired by the webcam into an angular scattering intensity profile that allows for distinguishing the sperm cells. Exposure parameters can be optimized depending on the laser power and the camera used. The processor may also be used to perform any comparisons between values to obtain approximations. A light block can be used to reduce or prevent the bleaching of the camera (i.e. obtaining an image with the laser directly on the camera which produces an overexposed image) when no sperm is in the path of the laser for scattering. Other detectors such as photodiodes or photodiode arrays, can also be used. Other processors associated with other detectors can also be used.

In the case where a webcam is used to acquire information, a module or engine can be employed to obtain an angular scattering intensity profile so that peaks caused by the sperm cells can be obtained. This module can be custom written or ImageJ open source software may be used and then executed via the processor.

The system also includes a first detection by the first scattered light detector of first scattered light data 14 (DSL$_1$). For the current disclosure, DSL$_1$ represents detected scattered light by the first detector. This scattered light is detected as a function of the angle of scattering and is synonymous with the phrases angular distribution or angular scattering intensity profile.

The first scattered light data (DSL$_1$) includes first incident light scattered by the passage of the sperm being tested into a preset angular range away from the first incident light central ray. The angular distribution of the scattering from the sperm cells includes the scattering from the nucleus of the sperm where there are differences in the nuclear material content of X sperm and Y sperm. There can be a preset intensity threshold for this detection to ensure that the test sperm is scattering the first incident light. Parts of the first incident light scattered beyond the first preset angular range can be sampled by the first scattered light detector to ensure that the scattering is by the test sperm rather than by some debris flowing along the sample container.

The first scattered light data (DSL$_1$) further includes a scattering profile with a scattering peak at an angle (TP$_1$) away from the first incident light central ray of first incident light scattered by the sperm being tested into the preset angular range away from the first incident light ray associated with the first detector. TP$_1$ is an abbreviation used to describe the angle at which a peak is observed on the acquired angular scattering intensity profile from the test sperm using the first detector. The system can also include of at least a second detector which allows for at least a second detection of the sperm in the form of a second scattered light data (DSL$_2$). The second scattered light data (DSL$_2$) includes a second scattering profile with a scattering peak at an angle (TP$_2$) away from the second incident light central ray of the second incident light scattered by the sperm being tested into the preset angular range away from the second incident light ray associated with the second detector. $TP_2$ is an abbreviation used to describe the angle at which a peak is observed on the acquired angular scattering intensity profile from the test sperm using the second detector.

Additional detectors can be added to better distinguish between X sperm and Y sperm or to increase the speed of detection.

With respect to the calibration of the system, each of the detectors of the system is calibrated so that the angular scattering intensity profile can be used to distinguish between the X sperm and the Y sperm.

The system is calibrated using a smaller sample of sperm from the sample of sperm being distinguished. This is recommended due to differences between sperm samples which have some variations especially if a sperm cell mixture from two or more males is to be sorted. Calibration also allows for the preset angular range to be properly set for sperm sample being distinguished from slight variations in sperm size distributions between animals as well as between species.

Figure 2:
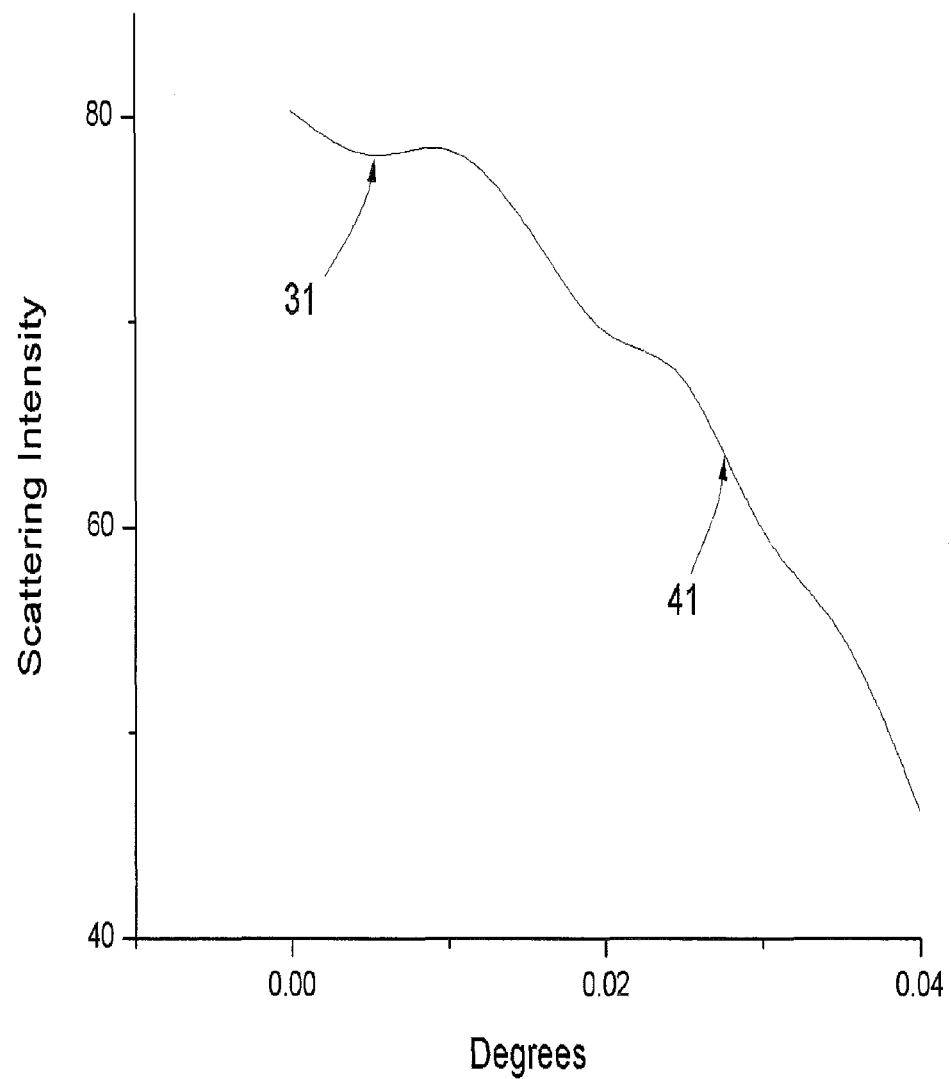
FIG. 2 shows calibration data with the approximate angle of an X-nucleus peak angle of incident light scattered by an X sperm nucleus and with the approximate angle of a Y-nucleus peak angle of incident light scattered by a Y sperm nucleus.

The angular distribution of the scattering from the sperm cells which contains peaks that are caused at the X-nucleus and Y-nucleus peak angles can be ascertained using this small sub-sample from which a calibration curve including of scattering profile can be produced. The peak angle can be defined in various ways. One example is the angle away from the first incident light central ray to the greatest intensity of the peak. The angular distribution can be obtained by averaging the angular scattering intensities as each sperm passes the incident light ray over the number of sperm cells. The averaged angular intensity scattering curve results in peaks from the X sperm and the Y sperm as shown in FIG. 2 which is the calibration curve. $CSL_1$ is an abbreviation used to describe the calibration curve from the scattering data from the first detector. The more the number of sperm that are used to generate the calibration curve, the better the signal-to-noise ratio and better the sperm from the sample can be distinguished.

The averaged angular intensity scattering curve can be used to generate calibration data 16 ($CSL_1$). The calibration data can be used to generate a calibration curve The first calibration data includes a first approximate X-nucleus peak angle 31 ($CX_1$) away from the first incident light central ray of first incident light scattered by nuclei of X sperm from the sample of sperm. Since the angular scattering intensity profile can be shown according to pixels on the webcam, actual pixel numbers can also be used instead of scattering angle for calibration and for distinguishing sperm. The first calibration data also includes a first approximate Y-nucleus peak angle 41 ($CY_1$) away from the first incident light central ray of first incident light scattered by nuclei of Y sperm from the sample of sperm.

At least $CX_1$ and $CY_1$ are included in the first preset angular range.

FIG. 2 shows typical first calibration data obtained by detecting with the first scattered light detector first incident light scattered in-turn by five thousand unsorted sperm flowing single-file in the sample container. $CX_1$ can be set just before the X sperm peak as indicated 31 and $CY_1$ can be set just after the Y sperm peak as indicated 41.

The system also includes a first comparison of first scattered light data ($DSL_1$) with first calibration data ($CSL_1$) to obtain a first approximation 15 ($A_1$) that the test sperm is an X sperm rather than an Y sperm:

$$A_1 = f_1(CSL_1, DSL_1).$$

In a multiple detection option the system can also comprise a second source of second incident light 21.

A multiple detection option can include positioning the test sperm in the first detection part of the sample container and re-positioning the test sperm in the detection part of the sample container by a micro-fluidic actuator. Other ways to vary orientation of the sperm relative to incident light and scattered light detection can be used.

The second incident light has a second incident light central ray which intersects the sample container 12.

The second incident light is positioned so that the test sperm nucleus scatters second incident light after the test sperm nucleus scatters first incident light.

The second incident light has a second incident light wavelength.

In an option, the second wavelength can be not equal to the first wavelength. In an option, the second wavelength can be equal to the first wavelength.

In this option the system can also include a second scattered light detector 23. The second scattered light detector is positioned to detect second incident light scattered by the test sperm nucleus.

The second scattered light detector and the first scattered light detector can be parts of one scattered light detector.

In the multiple detection option the system can also include a second detection by the second scattered light detector of second scattered light data 24 ($DSL_2$).

The second scattered light data ($DSL_2$) includes second incident light scattered by the nucleus of the test sperm into a second preset angular range away from the second incident light central ray.

The second scattered light data ($DSL_2$) further includes a second test sperm nucleus scattering peak angle ($TP_2$) away from the second incident light central ray of second incident light scattered by the test sperm nucleus.

In this option the system also includes second calibration data 26 ($CSL_2$).

The second calibration data includes a second approximate Y-nucleus peak angle ($CY_2$) away from the second incident light central ray of second incident light scattered by nuclei of Y sperm from the sample of sperm.

The second calibration data also includes a second approximate X-nucleus peak angle ($CX_2$) away from the second incident light central ray of second incident light scattered by nuclei of X sperm from the sample of sperm.

At least $CX_2$ and $CY_2$ are included in the second preset angular range

In this option the system can also include a second comparison of second scattered light data ($DSL_2$) with second calibration data ($CSL_2$) to obtain a second approximation 25 ($A_2$) that the test sperm is an X sperm rather than a Y sperm:

$$A_2 = f_2(CSL_2, DSL_2)$$

In this option the system also includes an improved approximation 17 ($A_2'$) that the sperm is an X sperm rather than a Y sperm obtained using:

$$A_2' = f'(A_2, A_2)$$

In an option the equation $$A_1 = f_1(CSL_1, DSL_1) \text{ is}$$

$$A_1 = (CY_1 - TP_1)/(CY_1 - CX_1).$$

When the approximation $A_1$ is greater than 0.5 it is likely that the test sperm is an X sperm rather than a Y sperm.

When $A_1$ is less than 0.5 it is likely that the test sperm is a Y sperm rather than an X sperm.

In an option the equation $$A_2 = f_2(CSL_2, DSL_2) \text{ is}$$

$$A_2 = (CY_2 - TY_2)/(CY_2 - CX_2); \text{ and the equation}$$

$$A_2' = f'(A_1, A_2) \text{ is}$$

$$A_2' = (A_1 * A_2)/[(A_1 * A_2) + (1 - A_1) * (1 - A_2)].$$

Sensitivity and reliability of this approximation and the probability that the approximation does distinguish an X sperm from a Y sperm can all be improved by increasing the number of detections of test sperm nucleus scattering peak angles ($TP_i$) for the test sperm and of the approximations ($A_i$) from each of the detections.

For n values of $A_i$ having an average value $A_{avg}$ greater than 0.5, with i being the number of values of $A_i$ greater than $A_{avg}$, with $r=|n-i|$, with $x=i-r+1$, and with $y=n-i-r$, then the probability P that the sperm is an X sperm can be approximated by:

$$P = A_{avg}^{\hat{}} x * (-A_{avg})^{\hat{}} y / [A_{avg}^{\hat{}} x * (1 - A_{avg})^{\hat{}} y + A_{avg}^{\hat{}} y * (1 - A_{avg})^{\hat{}} x].$$

Many sperm can flow single-file along the sample container so that each in-turn is a test sperm and the system can approximate for each that it is an X sperm rather than a Y sperm, and alternatively that it is a Y sperm rather than an X sperm.

Sperm likely to be X sperm according the approximation can be routed to an X sperm flow and sperm likely to be Y sperm according to the approximation can be routed to a Y sperm flow. Alternatively, unwanted sperm, such as those for which a satisfactory $A_{avg}$ cannot be determined or the gender is to be rejected, can be destroyed in the flow.

In an option the system can also include a first calibration detection by the first scattered light detector of the first calibration data ($CSL_1$).

The first calibration data includes a first average of first sperm scattered light scattered in-turn by nuclei of each member of a first plurality of un-sorted sperm from the sample of sperm flowing single-file, in the sample container.

In an option, the multiple detection option system can include a second calibration detection by the second scattered light detector of second calibration data ($CSL_2$).

The second calibration data includes a second average of second sperm scattered light scattered in-turn by nuclei of each member of a second plurality of un-sorted sperm from the sample of sperm flowing single-file in the sample container.

First calibration data depend on the configuration of the system and depend on differences in samples of sperm. Second calibration data depend on the configuration of the system and depend on the same differences in samples of sperm which effect first calibration data. If the system is configured such that second calibration data is redundant, then first calibration data can be used in place of second calibration data.

FIG. 2 shows the result of a first calibration detection. Scattered light intensities were detected in-turn by the first scattered light detector for five thousand unsorted sperm flowing single-file along the sample container. Reliability and sensitivity of locations of $CX_1$ and $CY_1$ and thus of the system can be improved by detecting ten times this number of sperm for the calibration data.

$CX_1$ and $CX_2$ can be set just before the approximate X-nuclei peaks. $CY_1$ and $CY_2$ can be set just after the approximate Y-nuclei peaks.

It should be noted that in the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

Embodiments of the disclosure or components thereof can be provided as or represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or controller to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor, controller or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

The invention claimed is:

1. An apparatus to distinguish an X sperm from a Y sperm, the apparatus comprising:
   a first source of first incident light,
      the first incident light having a first incident light central ray,
      the first incident light having a first incident light wavelength;
   a sample container to contain a test sperm from a sample of sperm;
      the test sperm and other sperm from the sample of sperm flowing single-file along the sample container,
      the test sperm having a nucleus,
      the sample container being traversed by the first incident light central ray,
   a first scattered light detector,
      the first scattered light detector positioned to detect first incident light scattered by the nucleus of the test sperm in the sample container, the detected first incident light seen as first scattered light data (DSL1);
      the first scattered light data (DSL1) being first incident light scattered by the nucleus of the test sperm into a first preset angular range away from the first incident light central ray, the first scattered light data (DSL1) comprising a first nucleus scattering peak angle (TP1) away from the first incident light central ray of first incident light scattered by the test sperm nucleus;

the first scattered light detector also detecting first calibration data (CSL1), the first calibration data (CSL1) comprising:

a first approximate Y-nucleus peak angle (CY1) away from the first light central ray of first incident light scattered in-turn by nuclei of Y sperm in the sample of sperm flowing single-file along the sample container, a first approximate X-nucleus peak angle (CX1) away from the first light central ray of first incident light scattered in-turn by nuclei of X sperm in the sample of sperm flowing single-file along the sample container, and at least CX1 and CY1 being included in the first preset angular range.

* * * * *